(12) United States Patent
Swerdlow et al.

(10) Patent No.: US 7,351,532 B2
(45) Date of Patent: Apr. 1, 2008

(54) DNA SEQUENCE ANALYSIS

(75) Inventors: Harold Philip Swerdlow, Walden (GB); Colin Barnes, Walden (GB); John Andrew Todd, Walden (GB); Richard Michael Durbin, Walden (GB)

(73) Assignee: Solexa Limited, Nr. Saffron Walden, Essex (GB)

( * ) Notice: Subject to any disclaimer, the term of this patent is extended or adjusted under 35 U.S.C. 154(b) by 124 days.

(21) Appl. No.: 10/547,062

(22) PCT Filed: Feb. 26, 2004

(86) PCT No.: PCT/GB2004/000770

§ 371 (c)(1),
(2), (4) Date: Aug. 25, 2005

(87) PCT Pub. No.: WO2004/076692

PCT Pub. Date: Sep. 10, 2004

(65) Prior Publication Data

US 2006/0246449 A1 Nov. 2, 2006

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.5

(58) Field of Classification Search .............. 435/6; 536/23.1, 24.3
See application file for complete search history.

(56) References Cited

U.S. PATENT DOCUMENTS

| | | | |
|---|---|---|---|
| 4,988,617 A * | 1/1991 | Landegren et al. | 435/6 |
| 5,476,930 A | 12/1995 | Letsinger et al. | |
| 5,846,719 A * | 12/1998 | Brenner et al. | 435/6 |
| 5,952,174 A * | 9/1999 | Nikiforov et al. | 435/6 |
| 6,787,308 B2 * | 9/2004 | Balasubramanian et al. | 435/6 |
| 2005/0287526 A1 * | 12/2005 | Landegren et al. | 435/6 |

FOREIGN PATENT DOCUMENTS

| | | |
|---|---|---|
| EP | 0 195277 | 9/1986 |
| WO | WO 95/21271 | 8/1995 |
| WO | WO 97/08344 | 3/1997 |
| WO | WO 01/57248 | 8/2001 |
| WO | WO 02/053778 | 7/2002 |
| WO | WO 02/061127 | 8/2002 |

OTHER PUBLICATIONS

Xu et al., High sequence fidelity in a non-enzymatic DNA autoligation reaction, Nucleic Acids Research, 27:875-881 (1999).

* cited by examiner

*Primary Examiner*—Ethan Whisenant
(74) *Attorney, Agent, or Firm*—Klauber & Jackson

(57) ABSTRACT

There is disclosed a method for determining the identity of one or more mutations or single nucleotide polymorphisms (SNPs) in a genome, comprising: a contacting a sample genome, under conditions which permit template dependant oligonucleotide ligation, with a plurality of different oligonucleotide molecules which comprise (i) a first set of oligonucleotides each comprising a sequence of nucleotides that is complementary to a region on said genome that includes a known SNP site and which oligonucleotides are complementary to said region other than at a base at or near the 5' end of said oligonucleotides that is to be tested for complementarity to a base at the SNP site, each of said oligonucleotides comprising a unique label to identify both the base to be tested and the position of the SNP to be scored, (ii) a second set of oligonucleotides each comprising a sequence of nucleotides complementary to a region on said target genome for hybridisation with said target genome adjacent the 5' end of an oligonucleotide of said first oligonucleotide set, and a surface capture moiety, a phosphate moiety being located at any of either the 5' end of said first set of oligonucleotides or the 3' end of said second set of oligonucleotides, any resulting ligated oligonucleotide being immobilised on a solid support via the surface capture moiety, b. analysing said solid support for the identity of one or more of said unique labels and comparing the defined bases in any of said immobilised oligonucleotides to those of the reference one or more SNPs.

11 Claims, 1 Drawing Sheet

DNA SEQUENCE ANALYSIS

CROSS REFERENCE TO RELATED APPLICATIONS

Figure 1:
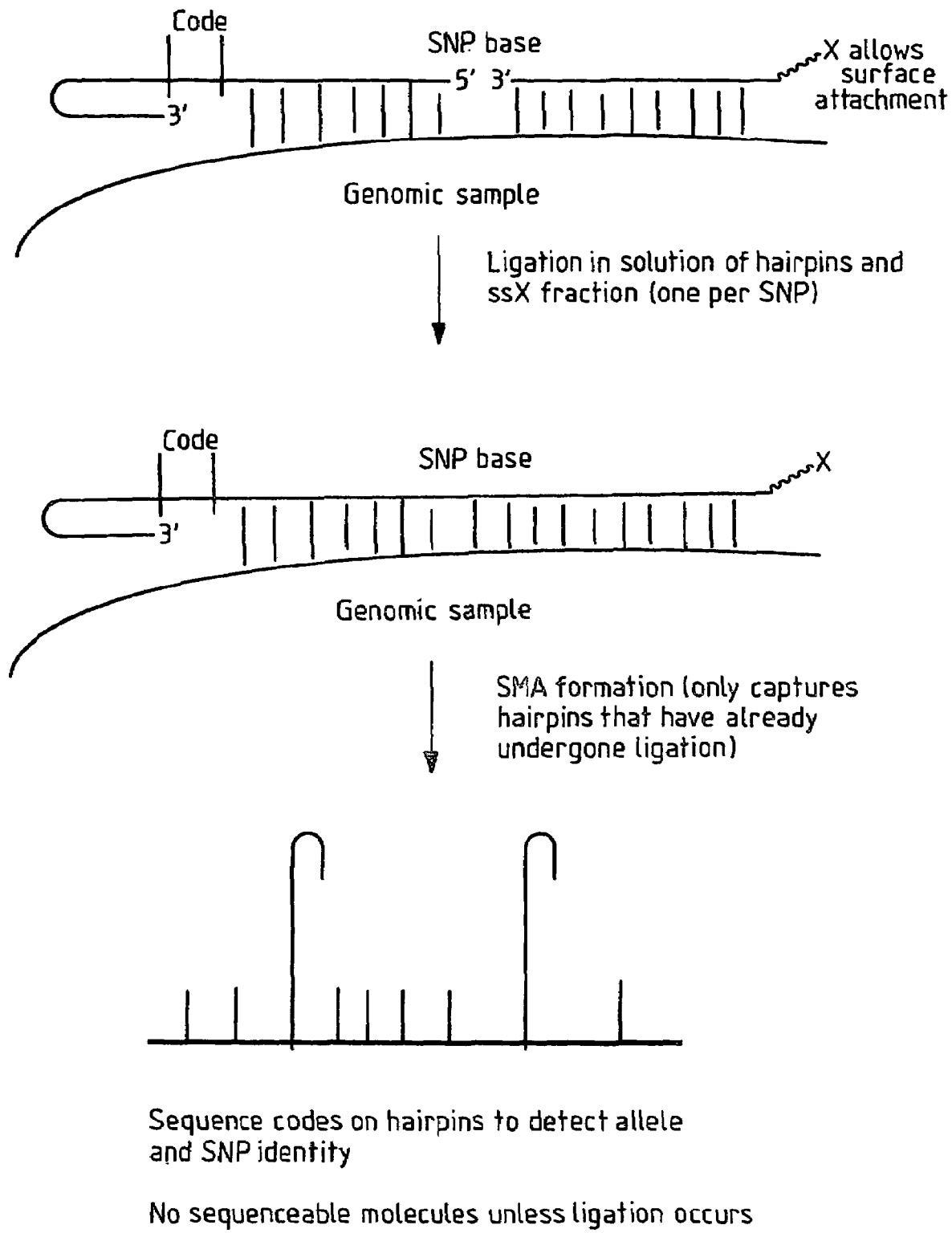

The present application is a National Stage Application claiming the priority of co-pending PCT Application No. PCT/GB2004/000770 filed Feb. 26, 2004, which in turn, claims priority from Great Britain Application Serial No. 0304371.8, filed Feb. 26, 2003. Applicants claim the benefits of 35 U.S.C. § 120 as to the PCT application and priority under 35 U.S.C. § 119 as to the said Great Britain application, and the entire disclosures of both applications are incorporated herein by reference in their entireties.

FIELD OF THE INVENTION

This invention relates to a method for detecting variations in the sequences of nucleic acid fragments, particularly in the DNA sequences of genes in a sample obtained from a patient.

BACKGROUND OF THE INVENTION

Recently, the Human Genome Project determined the entire sequence of the human genome—all $3 \times 10^9$ bases. The sequence information represents that of an average human. However, there is still considerable interest in identifying differences in the genetic sequence between different individuals. The most common form of genetic variation are single nucleotide polymorphisms (SNPs). On average one base in 1000 is a SNP, which means that there are 3 million SNPs for any individual. Some of the SNPs are in coding regions and produce proteins with different binding affinities or properties. Some are in regulatory regions and result in a different response to changes in levels of metabolites or messengers. SNPs are also found in non-coding regions, and these are also important as they may correlate with SNPs in coding or regulatory regions. The key problem is to develop a low cost way of determining one or more of the SNPs for an individual.

Nucleic acid arrays have been used to determine SNPs, usually in the context of monitoring hybridisation events (Mirzabekov, Trends in Biotechnology (1994) 12:27-32). Many of these hybridisation events are detected using fluorescent labels attached to nucleotides, the labels being detected using a sensitive fluorescent detector, e.g. a charge-coupled detector (CCD). The major disadvantage of these methods is that repeat sequences can lead to ambiguity in the results. This problem is recognised in Automation Technologies for Genome Characterisation, Wiley-Interscience (1997), ed. T. J. Beugelsdijk, Chapter 10: 205-225.

Other analysis methods require the sequencing of genomic fragments using high-density polynucleotide arrays. The use of high-density arrays in a multi-step analysis procedure can lead to problems with phasing. Phasing problems result from a loss in the synchronisation of a reaction step occurring on different molecules of the array. If some of the arrayed molecules fail to undergo a step in the procedure, subsequent results obtained for these molecules will no longer be in step with results obtained for the other arrayed molecules. The proportion of molecules out of phase will increase through successive steps and consequently the results detected will become ambiguous. This problem is recognised in the sequencing procedure described in U.S. Pat. No. 5,302,509.

An alternative sequencing approach is disclosed in EP-A-038 1693, which comprises hybridising a fluorescently labelled strand of DNA to a target DNA sample suspended in a flowing sample stream, and then using an exonuclease to cleave repeatedly the end base from the hybridised DNA. The cleaved bases are detected in sequential passage through a detector, allowing reconstruction of the base sequence of the DNA. Each of the different nucleotides has a distinct fluorescent label attached, which is detected by laser-induced fluorescence. This is a complex method, primarily because it is difficult to ensure that every nucleotide of the DNA strand is labelled and that this has been achieved with high fidelity to the original sequence.

SUMMARY OF THE INVENTION

The present invention is based on the realisation that the information provided by the Human Genome Sequencing Project can be used to design specific oligonucleotides that can be used to hybridise over a putative SNP site and in the presence of the correct DNA sequence undergo a template dependant ligation event. In the event that a first of the oligonucleotides includes at or near its 5' end a base complementary to the base at a SNP site, optionally with an associated phosphate, and the second oligonucleotide incorporates a surface capture moiety, in the presence of a DNA ligase these oligonucleotides may be joined to form a single ligated oligonucleotide that includes the surface capture moiety. The first oligonucleotide incorporates a unique label which may be in the form of a sequence code, identifying both the base near or at its 5' end and the position of the SNP to be scored in the genome, and therefore only those oligonucleotide molecules that have undergone the ligase reaction will be immobilised on a solid surface with the corresponding code. Analysing the label allows scoring and identification of the SNP site, which can then be compared with a reference sequence. A phosphate group is required for ligation of the oligonucleotides. This may also be located on the 3'-end of the second oligonucleotide rather than the 5'-end of the first. Furthermore, a non enzymatic chemical ligation may be used such as 5'-iodide with 3'-selenophosphate, within the context of the invention. Multiple oligonucleotides can be used in one experiment. This obviates the need to sequence the entire genome to identify multiple SNP sites, leading to a reduction in costs and processing time.

Therefore, according to a first aspect of the invention there is provided a method for determining the identity of one or more mutations or single nucleotide polymorphisms (SNPs) in a genome, comprising:

a. contacting a sample genome, under conditions which permit template dependant oligonucleotide ligation, with a plurality of different oligonucleotide molecules which comprise (i) a first set of oligonucleotides each comprising a sequence of nucleotides that is complementary to a region on said genome that includes a known SNP site and which oligonucleotides are complementary to said region other than at a base at or near the 5' end of said oligonucleotides in said first oligonucleotide set that is to be tested for complementarity to a base at the SNP site, each of said oligonucleotides comprising a unique label to identify both the base to be tested and the position of the SNP to be scored, (ii) a second set of oligonucleotides each comprising a sequence of nucleotides complementary to a region on said target genome for hybridisation with said target genome adjacent the 5' end of an oligonucleotide of said first oligonucleotide set, and a surface capture moiety, a phosphate moiety being located at any of either the 5' end of said first set of oligonucleotides or the 3' end of said second set of oligonucleotides, any resulting ligated oligonucleotide being immobilised on a solid support via the surface capture moiety, b. analysing said solid support for the identity of one or more of said unique labels and comparing the defined bases in any of said immobilised oligonucleotides to those of the reference one or more SNPs.

The method is particularly advantageous because only those first oligonucleotide molecules that incorporate a base that is complementary to the SNP in the sample genome, will undergo the ligation reaction with the second oligonucleotide incorporating the surface capture moiety for subsequent immobilisation on the solid surface. Accordingly, any ligated sequences immobilised on the solid surface may be analysed and compared to a reference sequence to establish whether the sample genome is the same as the reference sequence at the SNP. The method also renders it possible to establish if the SNP is homozygous or heterozygous for any SNP, the label being specific both for the base at the SNP and the position of the SNP in the genome.

FIG. 1 is a schematic view of a preferred embodiment of the method according to the invention.

DESCRIPTION OF THE INVENTION

The present invention relates to a method that can be used to identify SNP sites and particularly multiple SNP sites, in a target genome. The present invention is, therefore, useful to determine whether a subject has a particular SNP, and therefore a risk of disease. Many cancers are caused by genetic mutation on particular genes, for example a single mutation is implicated in breast cancer. The methods of the present invention can be used to screen for a wide variety of mutations that have been implicated in disease. The ability to screen for multiple (e.g. thousands) potential SNPs in a single experiment is therefore of great benefit.

The method relies on the ability to utilise the information provided by genome sequencing efforts, such as the Human Genome Project, to compare genomic sequences in a sample with a reference or wild-type sequence, to identify any aberrations. SNP sites are known and it is possible to use this information to design oligonucleotide molecules that are complementary to sequences on the genome immediately adjacent and overlapping the SNP site. The method of the invention relies on the design of two specific sets of oligonucleotides provided for hybridization on the sample genome overlapping the SNP and which undergo a ligation reaction only if the fully complementary sequence is present in the genomic sample. The first oligonucleotide set according to the invention, preferably includes a region complementary to the target genome up but not including the specific SNP site itself. Any resulting ligated oligonucleotide incorporates a unique label, such as for example a unique sequence, that can then be analysed following its immobilization on a solid surface. The unique label identifies both the SNP of the reference sequence and the position of the SNP in the genome. The immobilization occurs via a surface attachment moiety present on the oligonucleotide immediately 3' to the SNP which oligonucleotide does not include the SNP information.

The unique label or sequence code on the first oligonucleotide set is specific for both the defined base at or near the 5' end of the first oligonucleotide to be tested for complementarity with the base at the SNP site and the position of the SNP in question and renders it possible to identify multiple SNPs in the target genome. In the embodiment where the unique label comprises a unique sequence of nucleotides on the first oligonucleotide set, cycles of sequencing reactions may be carried out to identify the particular code on any oligonucleotide that is immobilised on the surface of the solid support. In this regard, it is particularly beneficial for the first oligonucleotide type to comprise a self priming hairpin oligonucleotide that forms a hairpin loop structure in which case only those hairpins immobilized on the solid surface will be able to undergo the sequencing reaction, The term "hairpin loop structure" refers to a molecular stem and loop structure formed from the hybridization of complementary polynucleotides that are covalently linked. The stem comprises the hybridized polynucleotides and the loop is the region that covalently links the two complementary polynucleotides. Anything from a 5 to 20 (or more) base pair double strand nucleic acid may be used to form the stem. In one embodiment, the structure may be formed from single-stranded polynucleotide complementary regions. The loop in this embodiment may be anything from two or more non-hybridised nucleotides. In a second embodiment, the structure is formed from two separate polynucleotides with complementary regions, the two polynucleotides being linked and the loop being at least partially formed from a linker moiety. The linker moiety forms a covalent attachment between the ends of the two polynucleotides. Linker moieties suitable for use in this embodiment will be apparent to the skilled practitioner. For example, the linker moiety may be polyethylene glycol (PEG).

In a preferred embodiment, the unique sequence code is located on the oligonucleotide to be proximal the hairpin so that only limited sequencing is required to sequence the code and thus establish both the identity of the defined base and the position of the SNP. It is particularly beneficial in the performance of the invention that the sequencing reaction is carried out on the known sequence of the oligonucleotide incorporating the hairpin because the order of the bases can be controlled so that the number of bases sequenced can be optimized. In a preferred embodiment, the assay will be multiplexed to identify thousands of SNPs.

The first oligonucleotide set therefore, may preferably, comprise a hairpin loop structure having a 5' phosphate, a defined base at or near, but preferably at the 5' end complementary to one of the heterozygotes under investigation and about 20 bases of sequence complementary to the genomic sample on the 5' side of the SNP together with the unique sequence code that identifies both the 20 bases of sequence, within the context of the other hairpins used in multiplexing, and the identity of the 5' base, and a self complementary loop that allows the free 3' hydroxyl to base pair adjacent to the start of the code.

The second oligonucleotide on the other hand may be a single stranded sequence of about 20 bases from the 3' side of the SNP complementary to the genomic sequence. The 3' hydroxyl end of this strand will be complementary to the genomic sample immediately adjacent to the 5'-end of the first oligonucleotide type. Because this sequence does not vary with heterozygosity only one such sequence type is required per assay. The 5' end of this oligonucleotide type contains a modification to allow surface attachment, for example biotin or thiophosphate. A variation on this method would be to locate the phosphate group on the 3'-hydroxyl of the second oligonucleotide instead of the 5'-position of the first oligonucleotide.

To establish heterozygosity of 1000 SNPs from a patient sample will require up to 5000 pieces of DNA, a hairpin oligonucleotide for each defined base at or near its 5' end and an oligonucleotide of the second type incorporating the surface capture moiety. The oligonucleotides are prepared prior to the assay and added to the sample genomic DNA along with a DNA ligase, such as T4 DNA ligase. The ligation reaction is allowed to proceed in solution then terminated by washing over a suitable capture surface such as a streptavidin slide. The sample is diluted prior to capture to allow formation of a single molecule array. Depending on heterozygosity, this process should give up to 2000 hairpins captured many times over the surface. Cycles of sequencing by synthesis may then be performed on any captured hairpins. The sequencing is performed to establish the identity of the codes. 1000 hairpins require 5 cycles ($4^5$) and a further cycle to call the SNP, i.e. the identity of the 5' base of the preligated hairpin.

The sample genomic DNA may be obtained by methods known in the art. In one embodiment, the genomic DNA may be fragmented prior to hybridization and ligation of the oligonucleotide molecules. Fragmentation may be carried out by any suitable method, including restriction enzyme digestion and/or the use of shear forces.

The oligonucleotides are preferably brought into contact with the fragments in solution under ligation conditions, so that duplex formation occurs between complementary oligonucleotide sequences and genomic fragments. Ligation conditions are known in the art and suitable buffers, salt concentrations, temperatures etc will all be apparent to the skilled person. After the ligation step, the resulting duplexes are immobilised onto a solid support.

Immobilisation of the ligated oligonucleotide molecule to the surface of a solid support may be carried out by techniques known in the art to form an array, which in one embodiment, as set out in more detail below, may provide adequate separation for individual resolution of the hairpin oligonucleotides. In the context of the present invention, an array refers to a population of polynucleotide molecules distributed over the solid support. Generally, the array is produced by dispensing small volumes of a sample to generate a random single molecule array. In this manner, a mixture of different molecules may be arrayed by simple means to produce a single molecule array. In this embodiment, both ligated and non-ligated oligonucleotides will be immobilised onto the solid support. However, those fragments that are not ligated to the hairpin oligonucleotide will not undergo the sequencing reaction and so will not generate a detectable signal.

The preligated oligonucleotide molecules contain a surface capture group that permits attachment to a complementary moiety on the surface of the solid support. This may be achieved by various techniques including, preferably, the incorporation of a nucleotide onto the 5' end of the second oligonucleotide type, the nucleotide being modified with a linker molecule that reacts with a suitably prepared solid support. The modified nucleotide can be incorporated onto the oligonucleotide in a conventional way using DNA synthesis or enzymatically using a terminal transferase. This incorporation step is carried out prior to the ligation step with the genomic sample.

Solid supports suitable for use in the invention are available commercially, and will be apparent to the skilled person. The supports may be manufactured from materials such as glass, ceramics, silica and silicon. The supports usually comprise a flat (planar) surface. Any suitable size may be used. For example, the supports might be of the order of 1 to 10 cm in each direction.

Immobilisation may be by specific covalent or non-covalent interactions. The oligonucleotide can be attached to the solid support at any position along its length, the attachment acting to tether the polynucleotide to the solid support. The immobilised oligonucleotide is then able to undergo the sequencing reaction. Immobilisation in this manner results in well separated single hairpin oligonucleotides.

After immobilisation, the incorporation of bases onto the hairpin self priming sequence can be determined, and this information used to identify the SNP present. Conventional assays, which rely on the detection of fluorescent labels attached to the bases, can be used to obtain the information on the SNP. These assays rely on the stepwise identification of suitably labelled bases, referred to as "single base" sequencing methods. The bases are incorporated onto the primer sequence using the polymerase reaction.

In an embodiment of the invention, the incorporation of bases is determined using fluorescently labelled nucleotides. The nascent chain (on the primer) is extended in a stepwise manner by the polymerase reaction. Each of the different nucleotides (A, T, G and C) incorporates a unique fluorophore and a group blocking the 3' position to prevent uncontrolled polymerisation. As used herein, the term "blocking group" refers to a moiety attached to a nucleotide which, while not interfering substantially with template-dependent enzymatic incorporation of the nucleotide into a polynucleotide chain, abrogates the ability of the incorporated nucleotide to serve as a substrate for further nucleotide addition. A "removable blocking group" is a blocking group that can be removed by a specific treatment that results in the cleavage of the covalent bond between the nucleotide and the blocking group. Specific treatments can be, for example, a photochemical, chemical or enzymatic treatment that results in the cleavage of the covalent bond between the nucleotide and the block. Removal of the blocking group will restore the ability of the incorporated, formerly blocked nucleotide to serve as a substrate for further enzymatic nucleotide additions.

The polymerase enzyme incorporates a nucleotide into the nascent chain complementary to the sequence on the hairpin oligonucleotide and the blocking group prevents further incorporation of nucleotides. Unincorporated nucleotides are removed and each incorporated nucleotide is "read" optically by a charge-coupled detector using laser excitation and filters. The 3'-blocking group is then removed (deprotected), to expose the nascent chain for further nucleotide incorporation. One advantage in the use of pre-designed sequencing codes is that the sequence can be set to contain no identical contiguous bases and therefore cycles of sequencing can optionally be performed using only one non-blocked nucleotide per cycle.

Because the array consists of distinct optically resolvable oligonucleotides, each target oligonucleotide will generate a series of distinct signals as the fluorescent events are detected. Details of the sequence are then determined and can be compared with known sequence information to identify SNPs.

The number of cycles that can be achieved is governed principally by the yield of the deprotection cycle. If deprotection fails in one cycle, it is possible that later deprotection and continued incorporation of nucleotides can be detected during the next cycle. Because the sequencing is performed at the single molecule level, the sequencing can be carried out on different oligonucleotide sequences at one time without the necessity for separation of the different sample fragments prior to sequencing. This sequencing also avoids the phasing problems associated with prior art methods.

The labeled nucleotides can comprise a separate label and removable blocking group, as will be appreciated by those skilled in the art. In this context, it will usually be necessary to remove both the blocking group and the label prior to further incorporation.

Deprotection can be carried out by chemical, photochemical or enzymatic reactions. A similar, and equally applicable, sequencing method is disclosed in EP-A-0640146. Other suitable sequencing procedures will be apparent to the skilled person.

The images and other information about the arrays, e.g. positional information, etc. are processed by a computer program which can perform image processing to reduce noise and increase signal or contrast, as is known in the art. The computer program can perform an optional alignment between images and/or cycles, extract the single molecule data from the images, correlate the data between images and cycles and specify the DNA sequence from the patterns of signal produced from the individual molecules.

In a preferred embodiment of the invention, the ligated hairpin oligonucleotide is immobilised on a solid support surface at a density that allows each oligonucleotide to be individually resolved by optical means, i.e. single molecule imaging. This means that, within the resolvable area of the particular imaging device used, there must be one or more distinct signals each representing one duplex. Typically, the detection of incorporated bases can be carried out using a single molecule fluorescence microscope equipped with a sensitive detector, e.g. a charge-coupled detector (CCD). Each duplex of the array may be analysed simultaneously or, by scanning the array, a fast sequential analysis can be performed. Methods for the preparation of single molecule arrays and for single molecule imaging are described in WO-A-00/06770.

The term "individually resolved" is used herein to indicate that, when visualised, it is possible to distinguish one duplex on the array from neighbouring duplexes. Visualisation may be effected by the use of the detectably-labelled nucleotides as discussed above.

The density of the arrays is not critical. However, the present invention can make use of a high density of immobilised molecules, and these are preferable. For example, arrays with a density of $10^6$ to $10^9$ molecules per $cm^2$ may be used. Preferably, the density is at least $10^7/cm^2$ and typically up to $10^8/cm^2$. These high density arrays are in contrast to other arrays which may be described in the art as "high density" but which are not necessarily as high and/or which do not allow single molecule resolution. On a given array, it is the number of single oligonucleotides, rather than the number of features, that is important. The concentration of nucleic acid molecules applied to the support can be adjusted in order to achieve the highest density of addressable single oligonucleotide molecules. At lower application concentrations, the resulting array will have a high proportion of addressable single oligonucleotide molecules at a relatively low density per unit area As the concentration of nucleic acid molecules is increased, the density of addressable single oligonucleotide molecules will increase, but the proportion of single oligonucleotide molecules capable of being addressed will actually decrease. One skilled in the art will therefore recognize that the highest density of addressable single oligonucleotide molecules can be achieved on an array with a lower proportion or percentage of single oligonucleotide molecules relative to an array with a high proportion of single oligonucleotide molecules but a lower physical density of those molecules.

Using the methods and apparatus of the present invention, it may be possible to image at least $10^7$ or $10^8$ molecules. Fast sequential imaging may be achieved using a scanning apparatus; shifting and transfer between images may allow higher numbers of hairpin oligonucleotide molecules to be imaged.

The extent of separation between the individual oligonucleotide molecules on the array will be determined, in part, by the particular technique used for resolution. Apparatus used to image molecular arrays are known to those skilled in the art. For example, a confocal scanning microscope may be used to scan the surface of the array with a laser to image directly a fluorophore incorporated on the individual molecule by fluorescence. Alternatively, a sensitive 2-D detector, such as a charge-coupled detector, can be used to provide a 2-D image representing the individual oligonucleotide molecules on the array.

Resolving single molecules on the array with a 2-D detector can be done if, at 100× magnification, adjacent oligonucleotide molecules are separated by a distance of approximately at least 250 nm, preferably at least 300 nm and more preferably at least 350 nm. It will be appreciated that these distances are dependent on magnification, and that other values can be determined accordingly, by one of ordinary skill in the art.

Other techniques such as scanning near-field optical microscopy (SNOM) are available which are capable of greater optical resolution, thereby permitting more dense arrays to be used. For example, using SNOM, adjacent oligonucleotide molecules may be separated by a distance of less than 100 nm, e.g. 10 nm. For a description of scanning near-field optical microscopy, see Moyer et al., Laser Focus World (1993) 29(10).

An additional technique that may be used is surface-specific total internal reflection fluorescence microscopy (TM); see, for example, Vale et al., Nature, (1996) 380: 451-453). Using this technique, it is possible to achieve wide-field imaging (up to 100 μm×100 μm) with single molecule sensitivity. This may allow arrays of greater than $10^7$ resolvable molecules per $cm^2$ to be used.

Additionally, the techniques of scanning tunnelling microscopy (Binnig et al., Helvetica Physica Acta (1982) 55:726-735) and atomic force microscopy (Hansma et al., Ann. Rev. Biophys. Biomol. Struct. (1994) 23:115-139) are suitable for imaging the arrays of the present invention. Other devices which do not rely on microscopy may also be used, provided that they are capable of imaging within discrete areas on a solid support.

As aforementioned, the target nucleic acid molecules immobilised onto the surface of the solid support should be capable of being resolved by optical means. This means that, within the resolvable area of the particular imaging device used, there must be one or more distinct signals, each representing one polynucleotide. Thus, each molecule is individually resolvable and detectable as a single molecule fluorescent point, and fluorescence from said single molecule fluorescent point also exhibits single step photobleaching.

Clusters of substantially identical molecules do not exhibit single point photobleaching under standard operating conditions used to detect/analyze molecules on arrays. The intensity of a single molecule fluorescence spot is constant for an anticipated period of time after which it disappears in a single step. In contrast, the intensity of a fluorescence spot comprised of two or more molecules, for example, disappears in two or more distinct and observable steps, as appropriate. The intensity of a fluorescence spot arising from a cluster consisting of thousands of similar molecules, such as those present on the arrays consisting of thousands of similar molecules at any given point, for example, would disappear in a pattern consistent with an exponential decay. The exponential decay pattern reflects the progressive loss of fluorescence by molecules present in the cluster and reveals that, over time, fewer and fewer molecules in the spot retain their fluorescence.

The sequence information obtained from the polymerase reaction can be compared to a reference sequence to identify the SNPs. The reference sequence is any suitable sequence that represents the normal/general genome. Suitable reference genomes have been identified as part of the various genome sequencing efforts, for example the Human Genome Project. It is, strictly, only the defined base at the SNP site that is compared with the corresponding base on the reference sequence. The additional sequenced bases in the unique sequence code are used to deconvolute the oligonucleotides and identify the relevant part of the reference sequence under study.

The invention claimed is:

1. A method for determining the identity of one or more mutations or single nucleotide polymorphisms (SNPs) in a genome, comprising:
   a. contacting a sample genome, under conditions which permit template dependent oligonucleotide ligation, with a plurality of different oligonucleotide molecules which comprise
      (i) a first set of at least two oligonucleotides, each comprising a sequence of nucleotides that is complementary to a region on said genome that includes a known SNP site, wherein a nucleotide complementary to the known SNP site is at or near the 5' end of each of said oligonucleotides and, each of said oligonucleotides further comprises a unique label which is a unique coding sequence of nucleotides, wherein said unique coding sequence of nucleotides is specific for the nucleotide complementary to the known SNP site and the position of the SNP to be scored,
      (ii) a second set of at least two oligonucleotides, each oligonucleotide comprising a sequence of nucleotides complementary to a region on said target genome for hybridisation with said target genome adjacent to the 5' end of an oligonucleotide of said first set of at least two oligonucleotides, and a surface capture moiety,
      a phosphate moiety being located at any of either the 5' end of said first set of at least two oligonucleotides or the 3' end of said second set of at least two oligonucleotides, wherein said contacting effects hybridization of the first and second set of at least two oligonucleotides to the sample genome and generates ligated oligonucleotides,
   b. immobilising the ligated oligonucleotides on a solid support via the surface capture moiety to generate immobilised ligated oligonucleotides,
   c. performing a sequencing reaction on the immobilised ligated oligonucleotides to determine at least the unique coding sequence of nucleotides of one or more of said unique labels, wherein determining the unique coding sequence of nucleotides of a unique label identifies the nucleotide complementary to the known SNP site and the position of the SNP to be scored, and comparing identified nucleotides complementary to known SNP sites in any of said immobilised oligonucleotides to those of one or more reference SNPs.

2. The method according to claim 1, wherein in step (a) each of said oligonucleotides in said first oligonucleotide set includes one of any of the defined nucleotide bases A, C, T or G for testing for complementarity with said SNP.

3. The method according to claim 1, wherein each of the oligonucleotides of said first oligonucleotide set includes a hairpin oligonucleotide.

4. The method according to claim 1 wherein said oligonucleotides are immobilised on said support at a density that allows each immobilised oligonucleotide to be individually resolved by optical microscopy.

5. The method according to claim 1 wherein the ligated product of said first and second sets of oligonucleotides comprises between 10 and 70 bases.

6. The method according to claim 1 wherein the ligated product of said first and second sets of oligonucleotide comprises from 30 to 50 bases.

7. The method according to claim 1, wherein said method is performed for a plurality of SNPs.

8. The method according to claim 1 wherein said sample genomic DNA is fragmented prior to contacting with said sets of oligonucleotides.

9. The method according to claim 1, wherein said oligonucleotides are contacted with said genome in the presence of a DNA ligase.

10. The method according to claim 1, wherein said first and second sets of oligonucleotides are contacted with said genome under conditions that permit non-enzymatic chemical ligation.

11. The method according to claim 10, wherein said oligonucleotides comprise 5'-iodide and 3'-selenophosphate.

* * * * *